(12) United States Patent
Katsnelson

(10) Patent No.: US 6,904,322 B2
(45) Date of Patent: Jun. 7, 2005

(54) TRANSCRANIAL ELECTROSTIMULATION APPARATUS AND METHOD

(75) Inventor: Yakov S. Katsnelson, Bronx, NY (US)

(73) Assignee: Kalaco Scientific, Inc., Scottsdale, AZ (US)

(*) Notice: Subject to any disclaimer, the term of this patent is extended or adjusted under 35 U.S.C. 154(b) by 533 days.

(21) Appl. No.: 10/075,675

(22) Filed: Feb. 15, 2002

(65) Prior Publication Data

US 2003/0158589 A1 Aug. 21, 2003

(51) Int. Cl.$^7$ ................................................ A61N 1/08
(52) U.S. Cl. ....................................... 607/72; 607/68
(58) Field of Search .......................... 607/72, 74, 68

(56) References Cited

U.S. PATENT DOCUMENTS

| | | | |
|---|---|---|---|
| 3,835,833 A | * | 9/1974 | Limoge ....................... 600/26 |
| 3,881,494 A | | 5/1975 | Paul |
| 4,071,033 A | | 1/1978 | Nawracaj |
| 4,121,594 A | * | 10/1978 | Miller et al. .................. 607/74 |
| 4,140,133 A | | 2/1979 | Kastrubin |
| 4,305,402 A | | 12/1981 | Katims |
| 4,327,322 A | | 4/1982 | Yukl |
| 4,352,351 A | | 10/1982 | Venin |
| 4,541,432 A | | 9/1985 | Molina-Negro |
| 4,582,063 A | | 4/1986 | Mickiewicz |
| 4,627,438 A | | 12/1986 | Liss |
| 4,646,744 A | | 3/1987 | Capel |
| 4,709,700 A | | 12/1987 | Hyrman |
| 4,754,759 A | | 7/1988 | Allocca |
| 4,821,723 A | * | 4/1989 | Baker et al. ................... 607/7 |
| 4,844,075 A | | 7/1989 | Liss |
| 4,922,908 A | | 5/1990 | Morawetz |
| 5,131,389 A | | 7/1992 | Giordani |
| 5,193,537 A | * | 3/1993 | Freeman ...................... 607/10 |
| 5,269,302 A | | 12/1993 | Swartz |
| 5,342,410 A | | 8/1994 | Braverman |
| 5,501,703 A | | 3/1996 | Holsheimer |
| 5,540,736 A | | 7/1996 | Haimovich |
| 5,643,330 A | | 7/1997 | Holsheimer |
| 5,776,170 A | | 7/1998 | MacDonald |
| 6,014,588 A | | 1/2000 | Fitz |
| 6,052,624 A | | 4/2000 | Mann |
| 6,161,044 A | | 12/2000 | Silverstone |
| 6,208,902 B1 | | 3/2001 | Boveja |
| 6,505,079 B1 | * | 1/2003 | Foster et al. .................. 607/68 |
| 6,591,138 B1 | * | 7/2003 | Fischell et al. ............... 607/45 |

FOREIGN PATENT DOCUMENTS

RU    2139111    5/1999

* cited by examiner

Primary Examiner—Lenwood Faulcon, Jr.
(74) Attorney, Agent, or Firm—LaValle D. Ptak

(57) ABSTRACT

Transcranial electrostimulation apparatus and method includes a first generator of bipolar pulses of a first predetermined frequency. A source of modulating control signals, producing an output at a second frequency less than the first predetermined frequency, is used to cause the output pulses from the first generator of pulses to vary in amplitude in a predetermined asymmetrical pattern at the frequency of the modulating control signals, with the asymmetrical pattern of signals applied to output electrodes designed to be attached to the scalp of a patient.

17 Claims, 2 Drawing Sheets

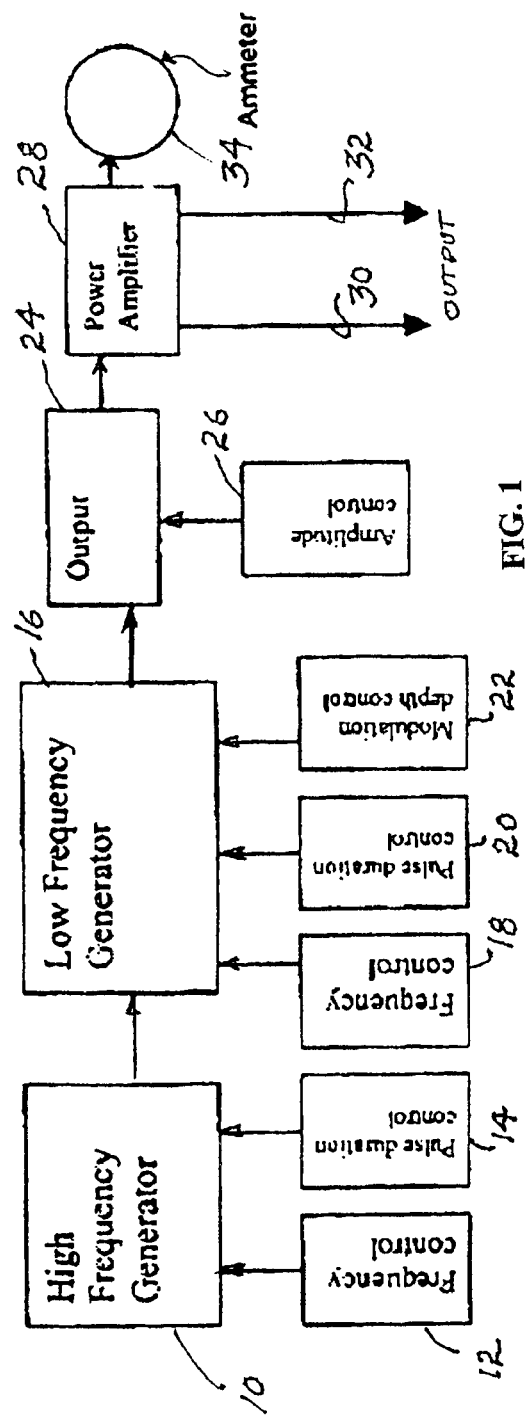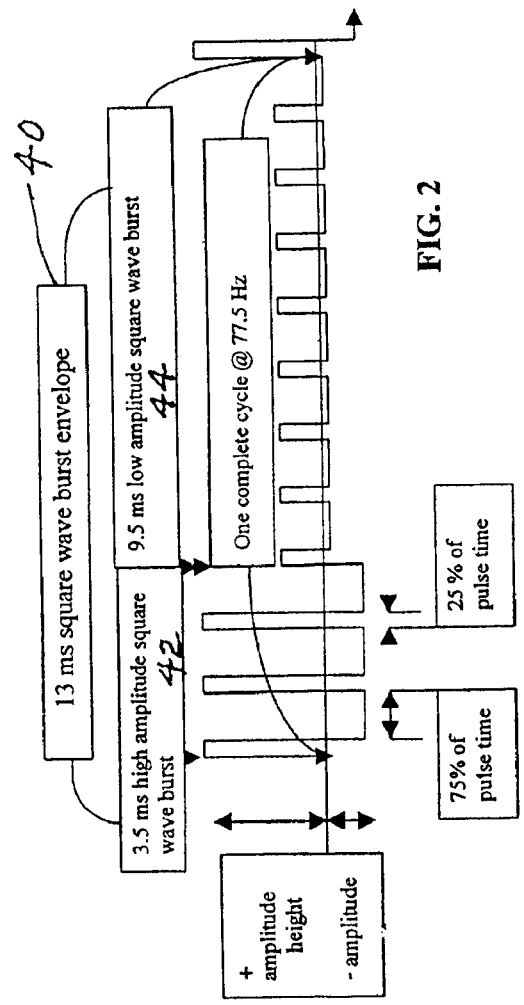

TRANSCRANIAL ELECTROSTIMULATION APPARATUS AND METHOD

BACKGROUND

Bio-electric stimulation apparatus has been developed for applying current pulses to a patient through electrodes located on opposite sides of the head of the patient. The current pulses at selected frequencies are applied to cause reaction with the central nervous system of the patient. Such devices, referred to as transcranial electrostimulation (TCES) or cranial electrostimulators (CES) have been used for a variety of non-invasive procedures, such as producing analgesic effects, reducing or controlling migraine headaches, and other applications of treatment and electro-anesthesia.

Earliest prototypes of transcranial electrostimulation devices originated in Russia. These original designs, although successfully employed for several different treatment modalities, had a severe drawback with regard to the comfort of the wearer or patient. In some cases, these earlier cranial electrostimulation devices even subjected the wearer to pain. It has been discovered that the reason for the discomfort of these earlier designs was a result of the use of direct current as part of the overall operation of the devices. The direct current was used to break down or lower skin resistance to allow the treatment alternating current signals to penetrate the brain and nervous systems to cause the desired effect established by the placement of the electrodes on the head of the patient.

In these earlier types of machines, the wearer received a combination of direct current and alternating current electrical waveform packages through a series of electrodes affixed to the head with straps. Typically, two electrodes comprising a cathode or negative pole of the DC based circuit would be placed approximately three inches apart to the left and right of the center of the forehead. Two other electrodes, comprising the anode of positive pole of the DC based circuit, were placed on the rear of the skull on the post mandibular area behind and below each ear.

With this DC current based design, the wearer was required to place a thick pad between any electrode and the skin. Typically, the pad was comprised of several layers of unbleached and uncolored cotton flannel, or an equivalent product. For best results, the fabric pads were soaked with water to provide a conductive path between the electrodes and the skin of the wearer. Without the presence of the pads (which were only required because of the presence of the DC current), such devices could either burn the skin of the wearer, or cause relatively intense pain before a usable level of the treatment modality of the currents at the AC frequency could be reached.

Although various types of treatment were employed by such earlier transcranial electrostimulation devices, the devices typically needed to be employed for an average time of thirty minutes per treatment period. Without the presence of the relatively thick cumbersome pads, the DC based design was unusable. With the presence of the thick padding, the DC design was bearable to the wearer, but rarely provided the wearer with a pleasant experience.

Three Russian patents which utilize such devices for different treatment methods comprise Russian patent Nos. 1489719; 1507404; and 1522500. In all of these patents, a combination of direct current and rectangular impulse current, with a frequency of between 70 and 80 Hertz, was employed at current amperages which were increased from a relatively low level to a higher or maximum level over the course of each treatment session.

An additional and potentially harmful drawback of the DC based designs was that of iontophoresis. A characteristic of a DC circuit application of this type is that molecular sized parts of metal, toxins and other undesirable impurities can be caused to migrate in the direction of current flow through the skin and into the bloodstream of the wearer of such DC based CES devices. Consequently, care had to be taken to ensure that no substance was present other than water used to create good electrical contact with the pad to the skin of the wearer. Since practically all CES treatment modalities require repeated treatments, the potential for iontophoresis being a harmful factor was escalated.

Transcranial electrostimulation (CES or TCES) originally was used in the 1960's to induce sleep; These early devices typically used less than 1.5 mA at 100 Hz. The Liss U.S. Pat. No. 4,627,438 employed higher frequencies modulated by a lower frequency squarewave to produce recurring pulse bursts. The repetition frequency of the device of Liss is determined by the modulation frequency; but the pulse bursts are of a uniform amplitude within each repetition cycle. The device of the Liss patent is specifically directed to utilization in conjunction with the treatment of migraine headaches. The low frequency or modulating signal is asymmetrical, utilizing a 3:1 duty cycle, "on" three-fourths of the time and "off" one fourth of the recurring period. This results in bursts of the high frequency signal separated by the off time when no signal is applied, following the re-application of the bursts of the high frequency signal. Some patient discomfort may be present in such an "on/off" system operation over the period of time of application of the pulse during a treatment interval.

A number of other United States patents, all directed to dual frequency systems which utilize high frequency signals modulated by a low frequency modulation carrier, operating in the general nature of the device of the Liss U.S. Pat. No. 4,627,438, exist. Typical of these patents are the patents to Limoge U.S. Pat. No. 3,835,833; Nawracaj U.S. Pat. No. 4,071,033; Kastrubin U.S. Pat. No. 4,140,133; Morawetz U.S. Pat. No. 4,922,908 and Giordani U.S. Pat. No. 5,131,389. All of these patents employ a uniform amplitude high frequency signal, which is modulated at the lower frequency of the modulation carrier.

A variation on the systems of the patents discussed above is disclosed in the Haimovich U.S. Pat. No. 5,540,736. The device of this patent employs two different current generators for providing electrical currents delivered to two electrode pairs operating across different portions of the head of the patient. This allows independent control of the current generators to administer independent regulated electrical current across each of the pairs to adjust for different impedances caused by the physiological and anatomical differences between different sides of a patient's mid brain portion, the quality of the conducting medium, and other factors. In all other respects, the system disclosed in this patent is similar to the operation of the system disclosed in the Liss patent discussed above.

Russian patent publication No. 2139111 is directed to a method for treating narcomania, which is a treatment also used in others of the CES patents described above for alcohol and narcotic addiction. In this patent, transcranial electrical stimulation is accomplished by means of packets of current with a duration of four milliseconds, at a modulation frequency of 100 Hz. Within each of the packets, the high frequency signals have a uniform frequency and current amplitude.

It is desirable to provide a transcranial electrostimulation apparatus and method which overcomes the disadvantages of the prior art, and which has increased effectiveness and increased user comfort.

SUMMARY OF THE INVENTION

It is an object of this invention to provide an improved transcranial electrostimulation apparatus and method.

It is an additional object of this invention to provide an improved transcranial electrostimulation apparatus and method which does not employ direct current components.

It is another object of this invention to provide an improved transcranial electrostimulation apparatus and method employing only alternating current components.

It is a further object of this invention to provide an improved transcranial electrostimulation apparatus and method utilizing packets or groups of high frequency pulses which vary amplitude within each of the packets in a uniform manner and in which the packets are repeated at a lower modulation frequency for application to electrodes for effecting transcranial electrostimulation.

In accordance with a preferred embodiment of the invention, a transcranial electrostimulation apparatus includes a first generator of bipolar pulses at a first predetermined frequency. A source of modulating control signals at a second frequency, which is less than the first predetermined frequency, is employed in conjunction with an amplitude control circuit receiving the pulses of the first predetermined frequency to produce bipolar pulses at the first predetermined frequency, which vary in amplitude in an asymmetrical pattern at the frequency of the modulating control signals.

BRIEF DESCRIPTION OF THE DRAWING

FIG. 1 is a diagrammatic drawing illustrating the overall principles of operation of the system in accordance with a preferred embodiment of the invention;

FIG. 2 is a waveform of a typical signal pattern of a preferred embodiment of the invention.

DETAILED DESCRIPTION

Figure 3:
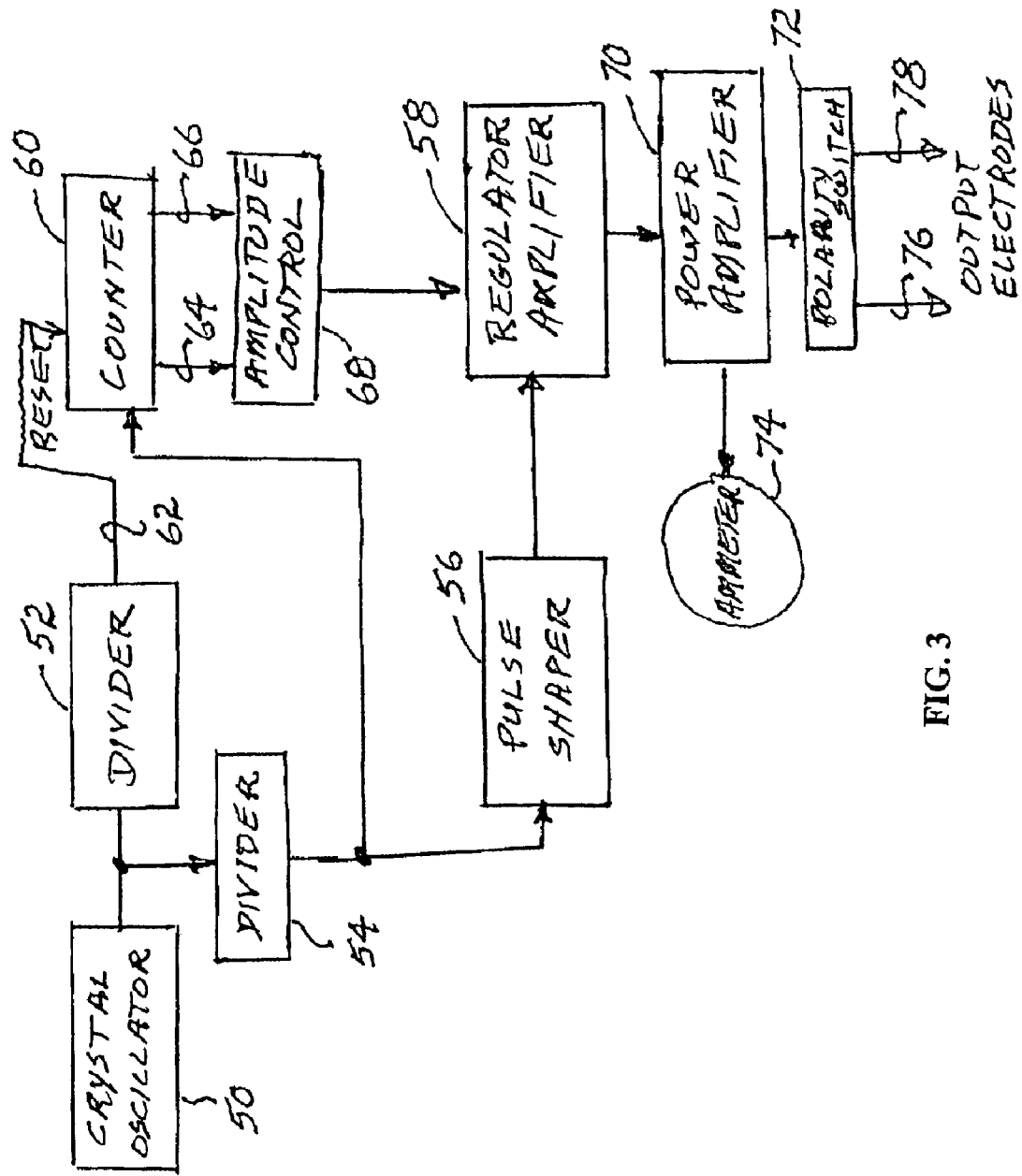
FIG. 3 is a block diagram of a system for producing the signals shown in FIG. 2.

Reference now should be made to the drawings which illustrate a preferred embodiment of the invention and its operation. FIG. 1 is a diagrammatic representation of the salient operating features of circuitry implementations which produce a unique triple waveform asymmetry useful for various transcranial electrostimulation applications. The unique waveform which is described in detail in conjunction with FIG. 2 produces little to no discomfort to the user of the device.

As illustrated in FIG. 1, the basic high frequency current signals are produced by a high frequency generator 10, which may employ a frequency control 12 and a pulse duration control 14 to establish the basic frequency and to provide the desired asymmetry between the positive and negative portions of each of the pulses produced by the generator 10. Typically, the generator 10 may include a crystal oscillator operating at 1,000 to 1,200 kHz, which then is divided down to the desired operating frequency of the alternating current pulses applied to the transcranial stimulation electrodes. Typically, the division ratio may be a 1:4 ratio to produce signals which then are modulated by a low frequency generator 16.

As illustrated in the diagrammatic representation of FIG. 1, the output of the low frequency generator 16 may be established by means of a conventional frequency control 18, a pulse duration control 20, and a modulation depth control 22 to produce a composite modulated output signal at 24, which comprises the pulses from the output of the high frequency generator 10 modulated by the low frequency generator 16. The output 24 then is provided with an amplitude control 26 to establish the amplitude of the pulse train supplied through the system to a power amplifier 28. The current at the power amplifier 28 may be varied in accordance with the treatment modality to be used by the system; and this current is measured by an ammeter 34. The power amplifier 28 then supplies appropriate transcranial alternating current pulses to a pair, or multiple pairs, of electrode outputs, illustrated as a single pair 30 and 32 in FIG. 1.

The operation of a preferred embodiment of the invention, for producing a waveform having triple asymmetry in order to produce effective transcranial electrostimulation, now should be considered in conjunction with the waveform of FIG. 2 and the block diagram of the system shown in FIG. 3. The block diagram of the system shown in FIG. 3 is typical of a manner of implementation of the various circuit functions required to produce the waveform of FIG. 2; but other arrangements for producing the signal waveform also may be utilized.

In FIG. 3, a crystal oscillator 50 is employed to provide the basic alternating current operating signals utilized for both the high frequency pulses and the modulating pulses illustrated in FIG. 1 as being produced by the high frequency generator 10 and the low frequency generator 16. Typically, the oscillator 50 may have an operating frequency in the order of 1,000 kHz to 1,200 kHz (although other frequencies may be used). The output of this oscillator is supplied to a divider 52, which may comprise multiple division stages, to produce the lower modulating frequency (illustrated in FIG. 1 as being generated by the low frequency generator 16). The output signals from the oscillator 50 also are supplied through a divider 54 to produce the operating signal waveform shown as the squarewave signal in the waveform of FIG. 2, after being shaped by a pulse shaper 56, to achieve the generally squarewave configuration of FIG. 2. In the example given, these pulses occur at an alternating current rate of 100 KHz; although they could be at higher or lower frequencies in accordance with particular applications of the system.

The pulses from the output of the divider 54 also are supplied to a counter 60, which may be of any suitable type such as a cascade counter or a ring counter, for producing outputs on leads 64 and 66 utilized in controlling the amplitude of the pulses from the pulse shaper 56. The counter 60 is reset by the output of the divider 52, applied over the lead 62, to reset the counter for each cycle of operation of the divider 52. In the present example, the output of the divider 52 (comprising the low frequency modulation control signal) is selected to be 77.5 Hz, since this repetition frequency has been found to be highly effective in conjunction with transcranial electrostimulation devices. Repetitive frequencies which are in the range of 70 Hz to 85 Hz have been found to be effective, but a frequency of 77.5 Hz has been empirically ascertained as a general ideal operating frequency for producing the maximum efficacy of the system.

The modulating or reset frequency, applied over the lead 62, could as well be supplied by a second independent crystal oscillator, operating at a lower initial frequency than the oscillator 50, if desired. If two different signal sources are employed, synchronization between the two should be effected to cause the various pulse transitions of the signals to be correlated with one another in order to produce the signal waveform of FIG. 2. The system shown in FIG. 3, however, is one effective way of accomplishing this.

Assume, for the present example, that the counter 60 has been reset to its initial or "zero" count. The system then operates to supply output pulses at the high frequency of the divided down signal from the divider 54 to the counter input, which advances one count for each of the applied pulses. In the waveform shown in FIG. 2, the initial pulses (the first four in FIG. 2) cause the counter outputs on 64 and 66 to be such that, as these outputs are applied to the amplitude control 68, a maximum amplitude (which may be adjusted if desired) is produced. This is illustrated in the left-hand portion of the waveform signal of FIG. 2. When pulse No. 4 in the group or packet is applied, a signal is obtained from one or both of the outputs 64 and 66 of the counter 60 and applied to the amplitude control circuit 68 to switch it to a lower amplitude, as illustrated for the right-hand portion of the signal shown in FIG. 2.

This causes the output of the amplitude control circuit 68 as applied to a regulator amplifier 58, to produce the signal waveforms in the asymmetrical pattern shown in FIG. 2, wherein the left-hand one-fourth (42) of each of the signal bursts is at a high amplitude; and the right-hand portion (44) comprising the remainder of the pulses is at a lower amplitude. The ratio is such that one-fourth (the initial amplitude) is at the high amplitude range, and that the remainder three-fourths is at the low amplitude range. This is the first level of asymmetry of the applied signals.

The regulator amplifier 58 also operates on the squarewave shaped pulses from the pulse shaper 56 to cause a second asymmetry in the positive and negative going aspects of the signal. As shown in FIG. 2, the negative going amplitude is one-fourth of the total excursion of the signal; and the positive going portion is three-fourths of the total excursion. This is true of both the maximum amplitude pulse 42 burst at the beginning of each of the burst groups or packets, and the lower amplitude portion 44 at the end of each of the burst groups or packets.

Finally, the third asymmetry is produced within the thirteen milisecond squarewave burst envelope illustrated as 40 in FIG. 2. This is the result of the operation of the divider signal on the lead 62 comprising the reset operation for the counter 60.

The composite asymmetrical signal illustrated in FIG. 2 then is provided by the output of the regular amplifier 58 to a power amplifier 70. The amplification may be adjusted to change the amount of current applied by the system (while maintaining the relative waveform shapes and patterns shown in FIG. 2) in accordance with the treatment modality to be utilized by users of the system. The ammeter 74 is employed to measure the magnitude of the current supplied by the system. It may be a simple analog ammeter, or it may be a digital ammeter providing separate readings of the maximum amplitude and minimum amplitude portions of the signal which is shown in FIG. 2.

The output of the amplifier 70 may be applied through a polarity switch 72 which allows the polarity of the signals applied to the spaced electrodes to be reversed, if desired. The polarity switch 72 supplies the signals across a pair of spaced output electrodes 76 and 78 which may in the form of pairs of split anodes and split cathodes, or which may be a single "anode" and "cathode" pair. Since no direct current components are present, the electrode paths connected to the outputs 76 and 78 are not really anodes and cathodes; but, depending upon the treatment which is being effected, it may be desirable to apply the positive going portions of the pulses to one or the other of these electrodes and the negative going portions to the other to achieve specific results.

It should be noted that in the system which is shown and described, there-are no direct current components. It also should be noted that although the system essentially is illustrating 70 kHz to 120 kHz tone bursts in each of the burst envelopes 40 shown in FIG. 2, other frequencies could be employed. As noted, the 77.5 Hz waveform, derived through the timing cycle, is used to complete each burst envelope including first pulses of a relatively high amplitude, followed by a series of pulses of a relatively low amplitude, in accordance with the signal pattern shown in FIG. 2. The frequency of pulse comprising the asymmetrical tone burst is approximately 1150 to 1450 times the repetition frequency of the burst envelopes.

In the system which is disclosed, an individual squarewave pulse of 0.01 Ms is utilized with 0.0075 Ms in the negative portion of the pulse and 0.0025 Ms in the positive portion of each of the pulses. The general asymmetrical waveform which is described above in conjunction with FIG. 2 has been found to be effective when it is centered around three-to-one ratios throughout the system operation. These ratios of course may be varied, in accordance with corresponding variations of other ratios of the system; but it has been found that the asymmetrical relationship which is disclosed replaces the formerly necessary, but unpleasant, DC portion of the operating protocol of earlier systems.

The DC current employed in some of the prior art devices was designed to provide a path penetrating the natural capacitive resistance of human skin. The DC current reduced the resistance to approximately 300 to 400 Ohms. The cost, however, was a high level of discomfort for the user of the device. It has been found that the utilization of the unique asymmetrical signal produced by the system shown in FIG. 3 and illustrated in the waveform of FIG. 2 effectively lowers the capacitive resistance of the epidermal layer to something on the order of 100 Ohms. Since less resistance is presented to the integrated 77.5 Hz modulating frequency, lower current levels are capable of achieving the same desired result which previously required much higher current levels. The lower current levels translate into a greater level of comfort for the patient or user of the device.

The foregoing description of the preferred embodiment of the invention is to be considered as illustrative and not as limiting. Various changes and modifications will occur to those skilled in the art for performing substantially the same function, in substantially the same way, to achieve substantially the same result without departing from the true scope of the invention as defined in the appended claims.

What is claimed is:

1. A method for effecting transcranial electrostimulation including the steps of:
   producing an asymmetrical tone burst envelope comprising a predetermined number of squarewave pulses, a first portion of which constitutes a high amplitude burst followed by a second portion which constitutes a low amplitude burst;
   repeating the asymmetrical tone burst successively at a repetition frequency that is between 70 Hertz and 85 Hertz; and
   delivering the repeated tone burst signals to electrodes of a transcranial electrostimulation apparatus.

2. The method according to claim 1 wherein the frequency of pulses comprising the asymmetrical tone burst is approximately 1150 to 1450 times the repetition frequency.

3. The method according to claim 1 wherein the duration of the high amplitude first portion of each tone burst is substantially twenty-five percent of the total duration of the tone burst.

4. The method according to claim 1 wherein the step of producing an asymmetrical tone burst includes producing a tone burst which is asymmetrical in amplitude and asymmetrical in the relative duration of the positive and negative portions of each complete cycle of the tone burst signal.

5. The method according to claim 4 wherein the ratio of the asymmetry of the amplitude of the first and second portions of the tone burst is substantially 1:3 and the duration of the positive and negative portions of each pulse of the tone burst also has a ratio of 1:3.

6. The method according to claim 5 wherein the frequency of pulses comprising the asymmetrical tone burst is approximately 1150 to 1450 times the repetition frequency.

7. The method according to claim 6 wherein the duration of the high amplitude first portion of each tone burst is substantially twenty-five percent of the total duration of the tone burst.

8. A transcranial electrostimulation apparatus including in combination:

a source of bipolar pulses of a first predetermined frequency;

source of modulating control signals to yield a second frequency which is less than said first predetermined frequency;

an amplitude control means responsive to the modulating control signals and coupled to the source of bipolar pulses at the first predetermined frequency for causing the amplitude of bipolar pulses in successive groups of bipolar pulses to vary in accordance with a predetermined asymmetrical pattern at the second frequency.

9. A transcranial electrostimulation apparatus according to claim 8 further including a pulse shaper coupled with the source of bipolar pulses of the first predetermined frequency to shape the dwell time of the bipolar pulses of the first predetermined frequency.

10. The transcranial electrostimulation apparatus according to claim 9 wherein the amplitude control means causes the bipolar pulses to have a greater amplitude in a first portion of each group of pulses and to have a lesser amplitude in a second portion of each group of pulses.

11. The transcranial electrostimulation apparatus according to claim 10 wherein the amplitude of the pulses in the first portion of each group of pulses has an amplitude substantially three times the amplitude of the pulses in the second portion.

12. A transcranial electrostimulation apparatus according to claim 11 including output electrodes coupled with the amplitude control means.

13. A transcranial electrostimulation apparatus according to claim 11 wherein the source of modulating control signals is a frequency divider coupled to the source of bipolar pulses of the first predetermined frequency.

14. The transcranial electrostimulation apparatus according to claim 8 wherein the amplitude control means causes the bipolar pulses to have a greater amplitude in a first portion of each group of pulses and to have a lesser amplitude in a second portion of each group of pulses.

15. The transcranial electrostimulation apparatus according to claim 14 wherein the amplitude of the pulses in the first portion of each group of pulses has an amplitude substantially three times the amplitude of the pulses in the second portion.

16. A transcranial electrostimulation apparatus according to claim 8 including output electrodes coupled with the amplitude control means.

17. A transcranial electrostimulation apparatus according to claim 8 wherein the source of modulating control signals is a frequency divider coupled to the source of bipolar pulses of the first predetermined frequency.

* * * * *